United States Patent
Furst

(10) Patent No.: US 10,453,269 B2
(45) Date of Patent: Oct. 22, 2019

(54) INTRAORAL SCANNING USING ULTRASOUND AND OPTICAL SCAN DATA

(71) Applicant: Align Technology, Inc., San Jose, CA (US)

(72) Inventor: Gilad Furst, Petach Tikva (IL)

(73) Assignee: Align Technology, Inc., San Jose, CA (US)

(*) Notice: Subject to any disclaimer, the term of this patent is extended or adjusted under 35 U.S.C. 154(b) by 127 days.

(21) Appl. No.: 14/563,714

(22) Filed: Dec. 8, 2014

(65) Prior Publication Data
US 2016/0163115 A1 Jun. 9, 2016

(51) Int. Cl.
| | |
|---|---|
| A61B 8/08 | (2006.01) |
| A61C 9/00 | (2006.01) |
| G06T 7/30 | (2017.01) |
| A61C 1/00 | (2006.01) |
| A61C 1/07 | (2006.01) |
| G06T 19/20 | (2011.01) |
| G06T 7/33 | (2017.01) |
| A61B 8/00 | (2006.01) |

(52) U.S. Cl.
CPC .......... *G06T 19/20* (2013.01); *A61B 8/5253* (2013.01); *A61B 8/5261* (2013.01); *A61C 9/0053* (2013.01); *A61C 9/0086* (2013.01); *G06T 7/344* (2017.01); *A61B 8/466* (2013.01); *G06T 2207/10136* (2013.01); *G06T 2207/20221* (2013.01); *G06T 2207/30036* (2013.01); *G06T 2210/41* (2013.01); *G06T 2219/2004* (2013.01); *G06T 2219/2016* (2013.01)

(58) Field of Classification Search
None
See application file for complete search history.

(56) References Cited

U.S. PATENT DOCUMENTS

| | | |
|---|---|---|
| 5,755,571 A | 5/1998 | Companion |
| 6,589,054 B2 | 7/2003 | Tingley et al. |
| 2005/0196028 A1* | 9/2005 | Kleen ............... A61B 8/483 382/128 |
| 2006/0072808 A1* | 4/2006 | Grimm ............. G06T 7/0028 382/151 |

(Continued)

FOREIGN PATENT DOCUMENTS

| | | |
|---|---|---|
| EP | 2671504 A2 | 12/2013 |
| WO | 2006/092800 A2 | 9/2006 |

OTHER PUBLICATIONS

D. A. Hughes et al., "5B-2 3D Imaging of Teeth Using High Frequency Ultrasound," Ultrasonics Symposium, 2007. IEEE, New York, NY, 2007, pp. 327-330.*

(Continued)

*Primary Examiner* — Jiangeng Sun
(74) *Attorney, Agent, or Firm* — Lowenstein Sandler LLP

(57) ABSTRACT

Optical scan data including a first set of images representing a first portion of a three-dimensional object is received. A processing device receives ultrasound scan data including a second set of three-dimensional images representing a second portion of the three-dimensional object. The processing device performs image stitching between the second set of three-dimensional images using the optical scan data. The processing device then creates a virtual model of the three-dimensional object based on the stitched second set of three-dimensional images.

3 Claims, 9 Drawing Sheets

(56) References Cited

U.S. PATENT DOCUMENTS

| | | | |
|---|---|---|---|
| 2006/0262970 A1* | 11/2006 | Boese | G03B 42/023 |
| | | | 382/131 |
| 2006/0270935 A1 | 11/2006 | Ariff et al. | |
| 2006/0281044 A1 | 12/2006 | Case et al. | |
| 2007/0083117 A1* | 4/2007 | Sakas | G01S 7/5205 |
| | | | 600/437 |
| 2008/0305458 A1 | 12/2008 | Lemchen | |
| 2009/0306506 A1* | 12/2009 | Heger | A61C 9/00 |
| | | | 600/443 |
| 2009/0306509 A1 | 12/2009 | Pedersen et al. | |
| 2010/0121191 A1 | 5/2010 | Ariff et al. | |
| 2010/0124732 A1 | 5/2010 | Ariff et al. | |
| 2010/0210943 A1 | 8/2010 | Mahmoud et al. | |
| 2011/0098572 A1* | 4/2011 | Chen | A61B 5/0062 |
| | | | 600/463 |
| 2012/0015316 A1* | 1/2012 | Sachdeva | A61C 5/40 |
| | | | 433/24 |
| 2013/0035596 A1* | 2/2013 | Ionasec | A61B 8/12 |
| | | | 600/450 |
| 2013/0329020 A1* | 12/2013 | Kriveshko | A61B 1/00009 |
| | | | 348/50 |
| 2014/0141385 A1* | 5/2014 | Taub | A61C 3/02 |
| | | | 433/27 |
| 2014/0187958 A1* | 7/2014 | Boutet | A61B 8/12 |
| | | | 600/462 |

OTHER PUBLICATIONS

Szopinski KT, Regulski P. Visibility of dental pulp spaces in dental ultrasound. Dentomaxillofacial Radiology. 2014;43(1):20130289. doi:10.1259/dmfr.20130289.*

Bains VK, Mohan R, Bains R. Application of ultrasound in periodontics: Part II. Journal of Indian Society of Periodontology. 2008;12(3):55-61. doi:10.4103/0972-124X.44096.*

S Logozzo, G Franceschini, A Kilpelä, M Caponi, L Governi, L Blois. A Comparative Analysis of Intraoral 3d Digital Scanners for Restorative Dentistry. The Internet Journal of Medical Technology. 2008 vol. 5 No. 1.*

Wang, Xueding et al. "Photoacoustic Imaging with a Commercial Ultrasound System and a Custom Probe." Ultrasound in medicine & biology 37.3 (2011): 484-492. PMC. Web. Nov. 21, 2017.*

International Search Report and Written Opinion of the International Searching Authority for PCT Application No. PCT/IB2015/059128 dated Feb. 25, 2016.

Heger, Stefan et al., "Accuracy assessment of high frequency 3D ultrasound for digital impression-taking of prepared teeth", Medical Imaging 2013, 10 pages, Ultrasonic Imaging, Tomography, and Therapy, Proc. of SPIE, vol. 8675, 86751N, downloaded from http://proceedings.spiedigitallibrary.org/ on Feb. 15, 2016.

Vollborn, Thorsten, et all, "A Voice-Coil Actuated Ultrasound Micro-Scanner for Intraoral High Resolution Impression Taking", Oct. 7-12, 2012, 6 pages, 2012 IEEE/R8J International Conference on Intelligent Robots and Systems, Vilamoura, Algarve, Portugal.

Poulsen, Carsten "Development of an Optical Positioning System for 3D Ultrasound—A Thesis Submitted to the Faculty of Worcester Polytechnic Institute in Partial Fulfillment of the Requirements for the Degree of Master of Science in Electrical and Computer Engineering," Oct. 2005.

Mahmoud et al., "High-Resolution 3D Ultrasound Jawbone Surface Imaging for Diagnosis of Periodontal Bony Defects: An In Vitro Study," Annals of Biomedical Engineering, vol. 38, No. 11, pp. 3409-3422, Nov. 2010.

Sharma et al., "Ultrasound as a Diagnostic Boon in Dentistry—A Review," International Jornal of Scientific Study, vol. 2, Issue 2, May 2014.

Marotti, J., et al. "Recent Advances of Ultrasound Imaging in Dentistry—A Review of the Literature (abstract only)," Oral Surg. Oral Med. Oral Pathol. Oral Radiol., Jun. 2014.

* cited by examiner

INTRAORAL SCANNING USING ULTRASOUND AND OPTICAL SCAN DATA

TECHNICAL FIELD

Embodiments of the present invention relate to the field of intraoral scanning and, in particular, to a system and method for using ultrasound and optical scan data in intraoral scanning.

BACKGROUND

In prosthodontic procedures designed to implant a dental prosthesis in the oral cavity, the dental site at which the prosthesis is to be implanted may be measured accurately and studied carefully, so that a prosthesis such as a crown, denture or bridge, for example, can be properly designed and dimensioned to fit in place. A good fit, for example, enables mechanical stresses to be properly transmitted between the prosthesis and the jaw and minimizes infection of the gums via the interface between the prosthesis and the dental site.

Some procedures call for removable prosthetics to be fabricated to replace one or more missing teeth, such as a partial or full denture, in which case the surface contours of the areas where the teeth are missing may be reproduced accurately so that the resulting prosthetic fits over the edentulous region with even pressure on the soft tissues.

In some practices, the dental site is prepared by a dental practitioner, and a positive physical model of the dental site is constructed. Alternatively, the dental site may be scanned to provide three-dimensional (3D) data of the dental site. In either case, the virtual or real model of the dental site may be sent to a dental lab that manufactures the prosthesis based on the model. However, if the model is deficient or undefined in certain areas, or if the preparation was not optimally configured for receiving the prosthesis, the design of the prosthesis may be less than optimal. For example, if the insertion path implied by the preparation for a closely-fitting coping would result in the prosthesis colliding with adjacent teeth, the coping geometry may need to be altered to avoid the collision. Further, if the area of the preparation containing a finish line lacks definition, it may not be possible to properly determine the finish line and thus the apical edge of the coping may not be properly designed. Indeed, in some circumstances, the model is rejected and the dental practitioner then re-scans the dental site, or reworks the preparation, so that a suitable prosthesis may be produced.

In orthodontic procedures, it can be important to provide a model of one or both dental arches and/or jaw. Where such orthodontic procedures are designed virtually, a virtual model of the oral cavity is also beneficial. Such a virtual model may be obtained by scanning the oral cavity directly, or by producing a physical model of the dentition, and then scanning the model with a suitable scanner.

Thus, in both prosthodontic and orthodontic procedures, obtaining a 3D model of a dental site in the oral cavity may be an initial procedure that is performed. When the 3D model is a virtual model, the more complete and accurate the scans of the dental site are, the higher the quality of the virtual model, and thus the greater the ability to design an optimal prosthesis or orthodontic treatment appliance.

BRIEF DESCRIPTION OF THE DRAWINGS

The present invention is illustrated by way of example, and not by way of limitation, in the figures of the accompanying drawings.

DETAILED DESCRIPTION

Figure 1:
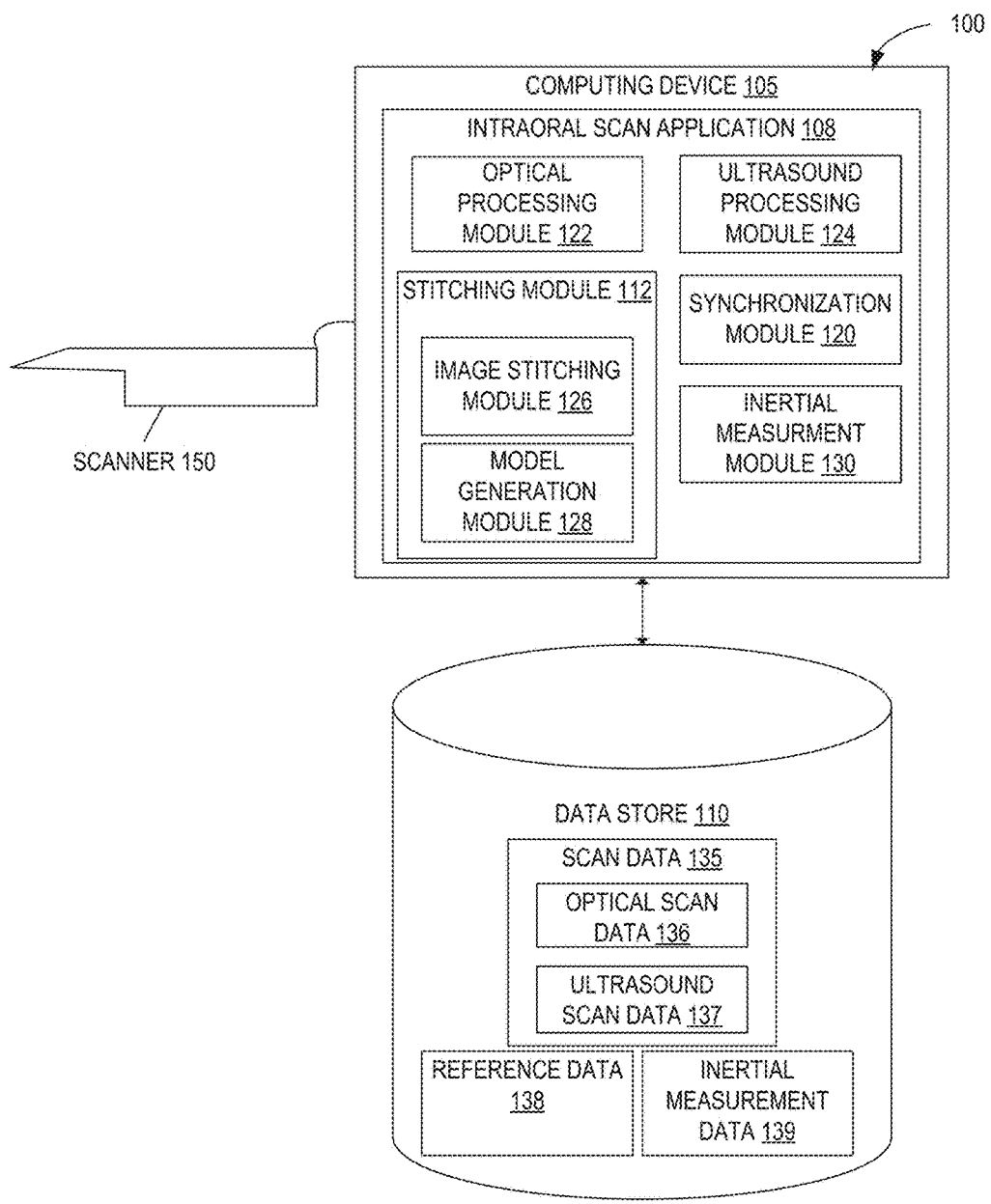
FIG. 1 illustrates a system for performing intraoral scanning using ultrasound and optical scan data and generating a virtual three dimensional model of a dental site, in accordance with embodiments of the present invention.

Described herein is a method and apparatus for improving the quality of scans, such as intraoral scans taken of dental sites for patients. During a scan session, a user (e.g., a dental practitioner) of a scanner may generate multiple different images (also referred to as scans) of a dental site, model of a dental site, or other object. The images may be discrete images (e.g., point-and-shoot images) or frames from a video (e.g., a continuous scan). Using only optical images may not capture all the areas of the dental site and typically may be limited to capturing areas above the gum line. In particular, features below the gum line, such as roots, jaw bone, gap between the roots and jaw bone, and an alveolar canal may be missing from optical images. Various x-ray technologies may be used to capture features below the gum line, such as cone beam computerized tomography (CBCT), but such x-ray technologies are expensive, large and cumbersome, and submit a patient to radiation exposure. Ultrasound imaging of dental sites may be radiation free, comparatively inexpensive, and provide resolution similar or better than CBCT. Ultrasound imaging for dental sites may have challenges. For example, ultrasound images may be inherently noisy. Additionally, in a dental setting a patient's jaw may move during the intraoral scan which may further contribute to noisy images. Noisy ultrasound images may make stitching together ultrasound images difficult and potentially unrepresentative of features of a dental site. The optical images may be precise and representative of features of the dental site. The capture of ultrasound images and optical images may be synchronized. Registration data from the optical images may be applied to the ultrasound images to address the difficulty of stitching noisy ultrasound images.

In one embodiment, an intraoral scan may be taken of a dental site for a patient. The intraoral scan may include optical scans of features above the gum line and ultrasound scans of features below the gum line. A probe containing both an optical sensor and ultrasound transducer may be used to capture the raw scan data. The optical and ultrasound scans may be synchronized. For example, an optical and ultrasound scan may be synchronized so that the optical scan may capture the crown of a tooth while the ultrasound scan may capture the root of the same tooth. Once both the optical and ultrasound raw scan data are processed into images, the optical images and ultrasound images may be registered and stitched together. For example, two optical images may be registered to determine rotations and translations for the optical images. Since the optical images may have corresponding synchronized ultrasound images from an ultrasound transducer having a known fixed offset from an optical sensor, the rotations and translations of the optical images may be applied to the corresponding ultrasound images. The optical and ultrasound images may be stitched together using the registration data and an accurate model of the dental site may be created.

Embodiments described herein are discussed with reference to intraoral scanners, intraoral images, intraoral scan sessions, and so forth. However, it should be understood that embodiments also apply to other types of scanners than intraoral scanners. Embodiments may apply to any type of scanner that takes multiple optical and ultrasound images and stitches these images together to form a combined image or virtual model. For example, embodiments may apply to desktop model scanners, and so forth. Additionally, it should be understood that the intraoral scanners or other scanners may be used to scan objects other than dental sites in an oral cavity. Accordingly, embodiments describing intraoral images should be understood as being generally applicable to any types of images generated by a scanner that contains both an ultrasound transducer and an optical sensor, embodiments describing intraoral scan sessions should be understood as being applicable to scan sessions for any type of object, and embodiments describing intraoral scanners should be understood as being generally applicable to many types of scanners.

FIG. 1 illustrates one embodiment of a system 100 for performing intraoral scanning using ultrasound and optical scan data and/or generating a virtual three dimensional model of a dental site. In one embodiment, system 100 carries out one or more operations of below described in methods 200, 400, and/or 500. System 100 includes a computing device 105 that may be coupled to a scanner 150 and/or a data store 110.

Computing device 105 may include a processing device, memory, secondary storage, one or more input devices (e.g., such as a keyboard, mouse, tablet, and so on), one or more output devices (e.g., a display, a printer, etc.), and/or other hardware components. Computing device 105 may be connected to a data store 110 either directly or via a network. The network may be a local area network (LAN), a public wide area network (WAN) (e.g., the Internet), a private WAN (e.g., an intranet), or a combination thereof. The computing device 105 may be integrated into the scanner 150 in some embodiments to improve performance and mobility.

Data store 110 may be an internal data store, or an external data store that is connected to computing device 105 directly or via a network. Examples of network data stores include a storage area network (SAN), a network attached storage (NAS), and a storage service provided by a cloud computing service provider. Data store 110 may include a file system, a database, or other data storage arrangement. Data store 110 may include scan data 135, reference data 138, and inertial measurement data 139. Inertial measurement data 139 may be data from inertial measurement module 130.

In some embodiments, a scanner 150 for obtaining three-dimensional (3D) and/or two-dimensional (2D) data of a dental site in a patient's oral cavity is operatively connected to the computing device 105. Scanner 150 may include a probe (e.g., a hand held probe) for optically and ultrasonically capturing three-dimensional structures (e.g., by confocal focusing of an array of light beams and by an ultrasound pulse-echo approach). Scanner 150 may include an optical sensor for optically capturing teeth or other visible structures. Scanner 150 may additionally include an ultrasound transducer for ultrasonically capturing features, such as features below the gum line such as roots, jaw bone, the gap between the root and jaw bone, and the alveolar canal.

The scanner 150 may be used to perform an intraoral scan of a patient's oral cavity. An intraoral scan application 108 running on computing device 105 may communicate with the scanner 150 to effectuate the intraoral scan. A result of the intraoral scan may be a sequence of intraoral images that have been discretely generated (e.g., by pressing on a "generate image" button of the scanner for each image) by, for example, optical processing module 122 and/or ultrasound processing module 124. The images may include optical images and/or ultrasound images of the patients oral cavity. Alternatively, a result of the intraoral scan may be one or more videos of the patient's oral cavity. An operator may start recording the video with the scanner 150 at a first position in the oral cavity, move the scanner 150 within the oral cavity to a second position while the video is being taken, and then stop recording the video. In some embodiments, recording may start automatically as the scanner identifies a tooth, root, or any other area of interest. The scanner 150 may transmit raw scan data to intraoral scan application 108. The raw scan data may include raw optical scan data and/or raw ultrasound scan data. Raw optical scan data may be processes by optical processing module 122 to generate discrete optical intraoral images or optical intraoral video. Raw ultrasound data may be processed by ultrasound processing module 124 to generate discrete ultrasound intraoral images or ultrasound intraoral video. Scan data 135 may include raw scan data, such as raw optical scan data and raw ultrasound scan data, and discrete images and/or intraoral video, such as discrete optical intraoral image, discrete ultrasound images, optical intraoral video, and/or ultrasound intraoral video. Optical scan data 136 may include any or all of optical scan data such as optical raw scan data, optical intraoral images, and optical intraoral video. Ultrasound scan data 137 may include any or all ultrasound scan data such as ultrasound raw scan data, ultrasound intraoral images, and ultrasound intraoral video. Scan data 135 may also be referred to collectively as image data images or intraoral images may refer to discrete images and/or intraoral video, such as discrete optical intraoral image, discrete ultrasound images, optical intraoral video, and/or ultrasound intraoral video. Computing device 105 may store the scan data 135 in data store 110. Alternatively, scanner 150 may be connected to another system that stores the image data in data store 110. In such an embodiment, scanner 150 may not be connected to computing device 105.

According to an example, a user (e.g., a practitioner) may subject a patient to intraoral scanning. In doing so, the user may apply scanner 150 to one or more patient intraoral locations. The scanning may be divided into one or more segments. As an example the segments may include a distal buccal region of the patient, a distal lingual region of the patient, a mesial buccal region of the patient, an mesial lingual region of the patient, one or more preparation teeth of the patient (e.g., teeth of the patient to which a dental device such as a crown or an orthodontic alignment device will be applied), one or more teeth which are contacts of preparation teeth (e.g., teeth not themselves subject to a dental device but which are located next to one or more such teeth or which interface with one or more such teeth upon mouth closure), patient bite (e.g., scanning performed with closure of the patient's mouth with scan being directed towards an interface area of the patient's superior jaw (e.g., upper teeth) and inferior jaw (e.g., lower teeth), and one or more root and/or jaw features associated with the aforementioned segments. Via such scanner application, the scanner 150 may provide image data (e.g., raw scan data) to computing device 105. The raw scan data may be processed to generate images (e.g., intraoral images) such as, 2D optical intraoral images, 3D optical intraoral images, 2D ultrasound intraoral images, and 3D ultrasound intraoral images. Optical raw scan data may be provided from scanner 105 to the computing device 105 in order for optical processing module 122 to generate optical images in the form of one or more points (e.g., one or more pixels and/or groups of pixels). For instance, the optical processing module 122 may generate a 2D or 3D optical image as one or more point clouds. In one embodiment, optical processing module 122 may be part of scanner 150 and scanner 150 may provide optical image to computing device 105. Ultrasound raw scan data may be provided from scanner 105 to the computing device 105 in order for ultrasound processing module 124 to generate a 2D or 3D ultrasound image. In one embodiment, ultrasound processing module 124 may be part of scanner 150 and scanner 150 may provide ultrasound images to computing device 105.

The manner in which the oral cavity of a patient is to be scanned may depend on the procedure to be applied thereto. For example, if a superior or inferior denture is to be created, then a full scan of the mandibular or maxillary edentulous arches as well as any associated features below the gum line (e.g., root and/or jaw features) may be performed. In contrast, if a bridge is to be created, then just a portion of a total arch and related features below the gum line may be scanned which may include an edentulous region, the neighboring abutment teeth and roots and the opposing arch and dentition. Thus, the dental practitioner may input the identity of a procedure to be performed into intraoral scan application 108. For this purpose, the dental practitioner may choose the procedure from a number of preset options on a drop-down menu or the like, from icons or via any other suitable graphical input interface. Alternatively, the identity of the procedure may be input in any other suitable way, for example by means of preset code, notation or any other suitable manner, intraoral scan application 108 having been suitably programmed to recognize the choice made by the user.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter aha, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances.

A type of scanner to be used may also be input into intraoral scan application 108, typically by a dental practitioner choosing one among a plurality of options. If the scanner 150 that is being used is not recognizable by intraoral scan application 108, it may nevertheless be possible to input operating parameters of the scanner thereto instead. For example, the optimal spacing between a head of the scanner and scanned surface can be provided, as well as the capture area (and shape thereof) of the dental surface capable of being scanned at this distance. Alternatively, other suitable scanning parameters may be provided. Scanner 150, according to one implementation, may be described in greater detail with respect to FIG. 3.

Referring back to FIG. 1, intraoral scan application 108 may identify spatial relationships that are suitable for scanning the dental site so that complete and accurate image data may be obtained for the procedure in question. Intraoral scan application 108 may establish an optimal manner for scanning a target area of the dental site.

Intraoral scan application 108 may identify or determine a scanning protocol by relating the type of scanner, resolution thereof, capture area at an optimal spacing between the scanner head and the dental surface to the target area, etc. For a point-and-shoot scanning mode, the scanning protocol includes a series of scanning stations spatially associated with the dental surfaces of the target area. Preferably, overlapping of the images or scans capable of being obtained at adjacent scanning stations is designed into the scanning protocol to enable accurate image registration, so that intraoral images can be stitched together to provide a composite 3D virtual model. For a continuous scanning mode (video scan), scanning stations may not be identified. Instead, a practitioner may activate the scanner and proceed to move the scanner within the oral cavity to capture a video of the target area from multiple different viewpoints.

In one embodiment, intraoral scan application 108 includes optical processing module 122, ultrasound processing module 124, stitching module 112, synchronization module 120, and inertial measurement module 130. Stitching module 112 may include image stitching module 126 and model generation module 128. Alternatively, the operations of one or more of the above-mentioned modules may be combined into a single module and/or divided into multiple modules.

Synchronization module 120 may synchronize the optical sensor and ultrasound transducer to obtain raw scan data at approximately the same time. An ultrasound image may correspond to an optical image when the generation of the raw scan data for the images is synchronized. The registration data from the registration of two optical images may be applied to corresponding ultrasound images. Registration data may include rotations and translations for the images on which registration may be performed. For example, by synchronizing the generation of raw data the optical image of a tooth may be registered and the registration data used to stitch together corresponding ultrasound images. Additionally, the optical images may be stitched together with the ultrasound images based on known fixed positional relationship between the optical sensor and the ultrasound transducer. Stitching may be the combination of two or more images (e.g., optical images, ultrasound images, or a combination of both) into a single image using registration data. In one embodiment, stitching includes applying the registration data from registering the optical images to the corresponding ultrasound images. The ultrasound image may be of the tooth's root and associated part of the jaw bone, while the optical image may be of a visible portion of the tooth that is above the gum line (e.g., the crown). Additionally, synchronization module 120 may use any number of compensation techniques in order to correct images for any asynchronous data collection.

Inertial measurement module 130 may receive raw inertial measurement data from an inertial measurement device in, for example, the probe of scanner 150. An inertial measurement device may include a combination of one or more accelerometers and/or one or more gyroscopes, that may help determine the probes velocity, orientation, and/or gravitational forces. Additionally, an inertial measurement device may include a magnetic sensor. A magnetic sensor may allow the inertial measurement device to determine the rotation position of the probe. Raw inertial measurement data may be processed from inertial measurement module 130 to help determine the orientation of scanner 150 during an intraoral scan. The orientation of the probe may be used to help determine additional registration data. Raw inertial measurement data and processed inertial measurement data may be referred to as inertial measurement data and be stored in inertial measurement data 139 of data store 110.

When a scan session is complete (e.g., all images for a dental site have been captured), stitching module 112 may generate a virtual 3D model of the scanned dental site. Alternatively, stitching module 112 may begin generating the virtual 3D model as the images are captured (e.g., before the scan session is complete). To generate the virtual model, image stitching module 126 may register the intraoral images generated from the intraoral scan session. In one embodiment, performing image stitching includes capturing 3D data of various points of a surface in multiple images (views from a camera), and registering the images by computing transformations between the images. The images may then be integrated into a common reference frame (e.g., "stitched" together) by applying appropriate transformations to points of each registered image.

In one embodiment, image stitching module 126 performing image stitching may include registering the optical images together and applying the registration data from registered optical images to the corresponding ultrasound images. Image stitching module 126 may determine that the optical sensor and the ultrasound transducer of scanner 150 have a fixed displacement from one another during an intraoral scan. Image stitching module 126 may register the optical images to determine optical registration information (e.g., registration data including rotations and translations). Additional ultrasound registration data may be determined for the ultrasound images by taking account of the fixed displacement and/or orientation of the ultrasound transducer from the optical transducer and modifying the corresponding optical registration data to account for the fixed displacement and/or orientation. Alternatively, the image registration data for a pair of optical images may be applied to the corresponding pair of ultrasound images without modification to the image registration data.

Image registration may be performed for each pair of adjacent or overlapping optical intraoral images (e.g., each successive frame of an intraoral video). Image registration algorithms are carried out to register two adjacent optical intraoral images, which essentially involves determination of the transformations which align one image with the other. Image stitching for ultrasound images may be performed based on the registration data obtained from registering the optical images. The registration data from registering the optical images may be applied to the ultrasound images to stitch the ultrasound images together and/or stitch the ultrasound images to the optical images. Each registration between a pair of images may be accurate to within 10-15 microns in one embodiment. Image registration may involve identifying multiple points in each image (e.g., point clouds) of an image pair, surface fitting to the points of each image, and using local searches around points to match points of the two adjacent images. For example, image stitching module 126 may match points of one image with the closest points interpolated on the surface of the other image, and iteratively minimize the distance between matched points. Image stitching module 126 may also find the best match of curvature features at points of one image with curvature features at points interpolated on the surface of the other image, without iteration. Image stitching module 126 may also find the best match of spin-image point features at points of one image with spin-image point features at points interpolated on the surface of the other image, without iteration. Other techniques that may be used for image registration include those based on determining point-to-point correspondences using other features and minimization of point-to-surface distances, for example. Other image registration techniques may also be used. The optical images and ultrasound images may also be stitched together based on a known offset and/or angle between the optical sensor and the ultrasound transducer in the scanner 150.

Many image registration algorithms perform the fitting of a surface to the points in adjacent images, which can be done in numerous ways. Parametric surfaces such as Bezier and B-Spline surfaces are most common, although others may be used. A single surface patch may be fit to all points of an image, or alternatively, separate surface patches may be fit to any number of a subset of points of the image. Separate surface patches may be fit to have common boundaries or they may be fit to overlap. Surfaces or surface patches may be fit to interpolate multiple points by using a control-point net having the same number of points as a grid of points being fit, or the surface may approximate the points by using a control-point net which has fewer number of control points than the grid of points being fit. Various matching techniques may also be employed by the image registration algorithms.

In one embodiment, image stitching module 126 may determine a point match between images, which may take the form of a two dimensional (2D) curvature array. A local search for a matching point feature in a corresponding surface patch of an adjacent image is carried out by computing features at points sampled in a region surrounding the parametrically similar point. Once corresponding point sets are determined between surface patches of the two images, determination of the transformation between the two sets of corresponding points in two coordinate frames can be solved. Essentially, an image registration algorithm may compute a transformation between two adjacent images that will minimize the distances between points on one surface, and the closest points to them found in the interpolated region on the other image surface used as a reference.

Image stitching module 126 repeats image registration for all adjacent image pairs of a sequence of intraoral images to obtain a transformation between each pair of images, to register each image with the previous one. For each optical image pair, the set of transformations (e.g., registration data including rotations and translations) that achieve the image registration are recorded and then applied (e.g., stitched) to the corresponding pair of ultrasound images. The set of transformations may or may not be modified based on known offset and/or angle differences between the optical sensor and the ultrasound transducer of the scanner 150. Although registering adjacent optical images is discussed, it should be appreciated that an adjacent image pair may include an optical image pair, an ultrasound image pair, and/or and an optical and ultrasound image pair. Image stitching module 126 then stitches all images together by applying the appropriate determined transformations to each of the optical images and/or ultrasound images. Once the images are stitched together the resulting 3D data may be merged to create a single virtual 3D model. Merging may be the smoothing of the resulting 3D data to create a single contiguous virtual 3D model. Merging may be performed by model generation module 128. As discussed above, in one embodiment the registration data from the optical images is applied to the corresponding ultrasound images. In another embodiment, the optical registration data is modified to account for the fixed displacement between the optical sensor and ultrasound transducer then applied to the corresponding ultrasound images. Each transformation may include rotations about one to three axes and translations within one to three planes.

In another embodiment, image stitching module 126 may register intraoral images by registering 2D or 3D optical images to a pre-existing model. Registering the optical images may include registering the first intraoral image using at least a portion of a pre-existing model and registering a second intraoral image using at least a portion of the pre-existing model. Rotations and translation may be determined based on registering the optical images to the pre-existing model. The registration process may be similar to the process discussed above. The rotations and translations determined from registering the optical images may be applied to the ultrasound images in a stitching process in a similar manner as discussed above. The stitched optical and ultrasound images may be merged and a virtual model may be created from the merged 3D data (e.g., merged image).

The pre-existing model may include a 3D model of the target dental site and be generated by data stored in reference data 138. Reference data 138 may include past data regarding the at-hand patient (e.g., intraoral images and/or virtual 3D models), some or all of which may be stored in data store 110. The data regarding the at-hand patient may include X-rays, 2D intraoral images, 3D intraoral images, 2D models, and/or virtual 3D models corresponding to the patient visit during which the scanning occurs. The data regarding the at-hand patient may additionally include past X-rays, 2D intraoral images, 3D intraoral images, 2D models, and/or virtual 3D models of the patient (e.g., corresponding to past visits of the patient and/or to dental records of the patient). The reference data 138 may be pooled patient data and may include X-rays, 2D intraoral images, 3D intraoral images, 2D models, and/or virtual 3D models regarding a multitude of patients. The reference data 138 may include pedagogical patient data. The pedagogical patient data may include X-rays, 2D intraoral images, 3D intraoral images, 2D models, virtual 3D models, and/or medical illustrations (e.g., medical illustration drawings and/or other images) employed in educational contexts. The pedagogical patient data may include volunteer data and/or cadaveric data.

Figure 2:
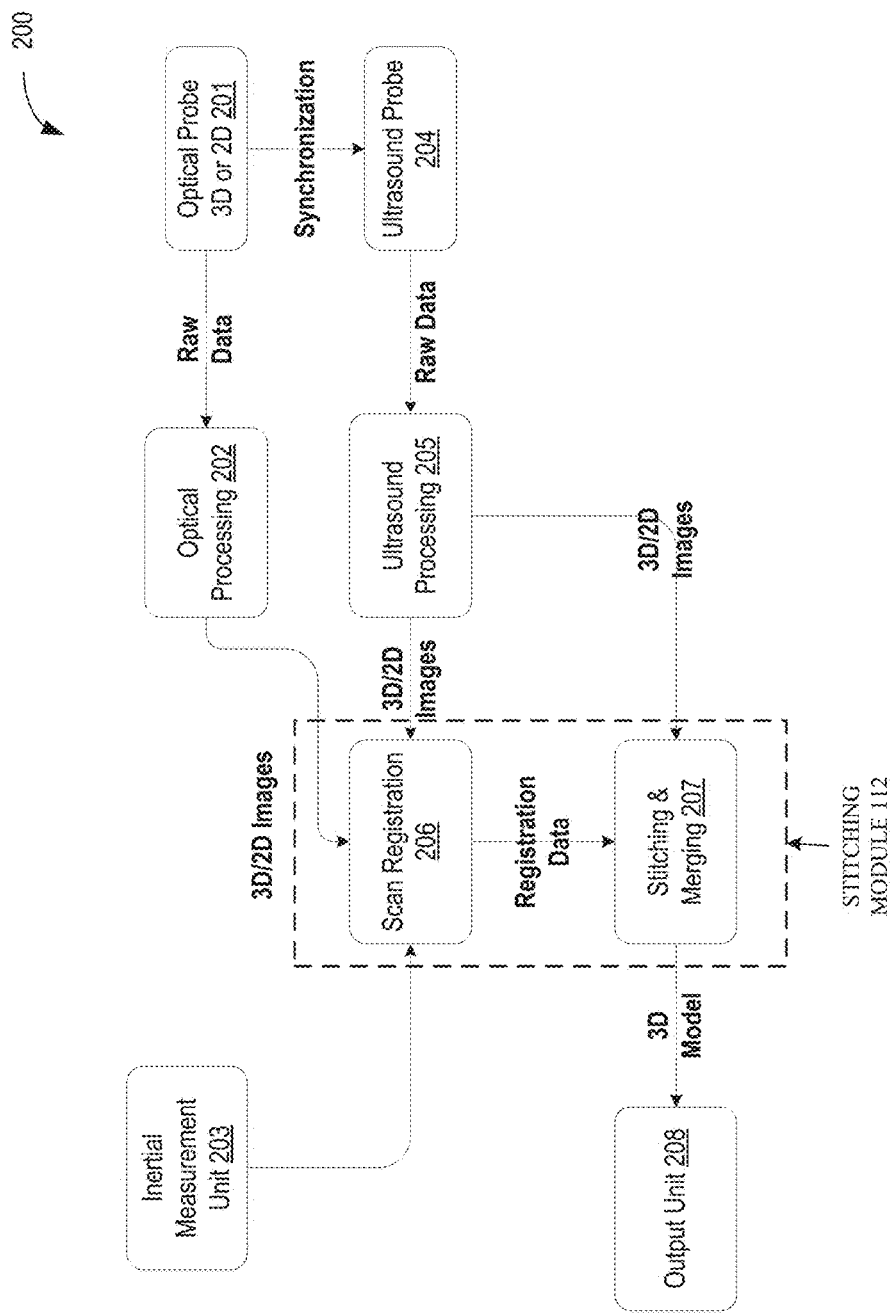
FIG. 2 illustrates a flow diagram for a method of performing intraoral scanning using ultrasound and optical scan data and generating a virtual three dimensional model of a dental site, in accordance with embodiments of the present invention.

FIG. 2 illustrates a flow diagram for a method of performing intraoral scanning using ultrasound and optical scan data and generating a virtual three dimensional model of a dental site, in accordance with embodiments of the present invention. Method 200 may be performed by processing logic that may comprise hardware (e.g., circuitry, dedicated logic, programmable logic, microcode, etc.), software (such as instructions run on a processing device), firmware, or a combination thereof. In one implementation, method 200 may be performed by system 100 of FIG. 1. In another implementation, method 200 may be performed or caused to be performed all or in part by stitching module 112 or intraoral scan application 108 of FIG. 1. For simplicity of explanation, method 200 is depicted and described as a series of acts. However, acts in accordance with this disclosure can occur in various orders, concurrently, and/or with other acts not presented or described herein. Furthermore, not all illustrated acts may be required to implement method 200 in accordance with the disclosed subject matter. In addition, those skilled in the art will understand and appreciate that method 200 may alternatively be represented as a series of interrelated states via a state diagram or interrelated events.

Method 200 begins at block 201 where processing logic implementing the method may generate and obtain raw optical scan data from an optical sensor attached to an optical probe. The optical probe may be part of scanner 150. The raw optical scan data may be 3D optical scan data or 2D optical scan data. The optical probe may be synchronized with the ultrasound probe in block 204 so that the ultrasound probe 204 generates ultrasound scans synchronously to the generation of the optical scans (e.g., so that the separate scans may occur simultaneously). The optical probe and ultrasound probe may be in the same probe or in different probes. The optical probe (i.e., optical sensor) and the ultrasound probe (i.e., ultrasound transducer) may be disposed in the probe with a fixed displacement between the two so that they move together during an intraoral scan.

Method 200 continues to block 202 where processing logic implementing the method processes the raw optical scan data to generate 2D or 3D optical images. Optical processing to generate optical images may be discussed in more detail with respect to FIGS. 1 and 3.

At the time of generating the optical scans (block 201) and ultrasound scans (block 204), an inertial measurement unit 203 may collect raw inertial measurement data of the optical and ultrasound probe. The inertial measurement unit 203 may include an inertial measurement sensor, an inertial measurement module, and inertial measurement data. The inertial measurement unit 203 may be located in the ultrasound probe, optical probe, or scanner 150. The raw inertial measurement data may be processed by inertial measurement unit to determine the orientation of scanner 150, and more specifically the orientation of the optical probe and ultrasound probe. The orientation information may be used as an additional data point to aid in image registration, and the optical images and ultrasound images may be more accurately registered together. The collection of raw inertial measurement data may be synchronized with the intraoral scanning, such as with the optical scan and ultrasound scan.

As mentioned, at block 204 processing logic generates and obtains raw ultrasound scan data from an ultrasound transducer attached to an ultrasound probe. The raw optical scan data may be 3D ultrasound scan data or 2D ultrasound scan data. The ultrasound probe may be synchronized with the optical probe in block 201, as discussed above. Blocks 201 and 204 may be performed synchronously, so that the optical and ultrasound scans may occur approximately simultaneously (e.g., accounting for differing measuring speeds of the optical probe verses the ultrasound probe).

Method 200 continues to block 205 where processing logic implementing the method processes the raw ultrasound scan data to generate 2D or 3D ultrasound images. Ultrasound processing to generate ultrasound images may be discussed in more detail with respect to FIGS. 1 and 3.

Method 200 continues to block 206 where processing logic implementing the method receives optical images and ultrasound images. The optical images may be used to produce registration information (i.e., registration data), such as rotations and translations. In one embodiment, the ultrasound images may be used to produce additional registration information. Further information, such as scanner orientation, may be received from the inertial measurement unit in block 203. In another embodiment, optical images may be registered to a pre-existing model, as discussed in regards to FIG. 1, to produce registration data. For example, 2D optical images may be taken, and may be registered against a virtual 3D model of a patient's dental arch to generate the registration data.

Method 200 continues to block 207 where processing logic implementing the method may stitch and merge the optical and/or ultrasound images as discussed above with reference to FIG. 1. Using the registration data received at block 206, the optical and/or ultrasound images may be stitched together to form an image that includes features above and below the gum line at block 207. The optical scan data (e.g., optical images) as discussed in reference to block 202 may be sent to block 207 from block 202 and/or block 206. Registration data based on the optical scan data may be used to stitch together the optical images at block 207. Additionally, the registration data based on the optical scan data may be used to stitch together the ultrasound images. Once separate image are stitched together, the resulting 3D data may be merged (e.g., smoothed) to create a 3D virtual model.

In an alternative embodiment, the ultrasound images may be registered and stitched together without the use of registration information from the optical images, as illustrated in FIG. 2 by the ultrasound images being sent directly to block 207 from block 205. Registration data may be generated for the ultrasound images themselves. Additional registration data for the ultrasound images may be generated by the inertial measurement unit, as described in block 203. The ultrasound images may be stitched together using the registration data. Additionally, the optical images may be stitched to the ultrasound images using the registration data generated from the ultrasound images and/or inertial measurement unit.

In another embodiment, the optical sensor as described in reference to block 201 and the ultrasound transducer as described in reference to block 204 may be in different probes and/or not synchronized. In such a case, a fiducial may be used in conjunction with an optical scan and an ultrasound scan. A fiducial may be an object placed in the field of view of an imaging system, such as an optical probe and/or an ultrasound probe, which appears in the image produced. The fiducial may be used as a point of reference or a measure. For example, a fiducial may be a powder that includes particles that reflect light and may be detected by an optical probe and an ultrasound probe. A fiducial may be an adhesive object that may be place at the dental site and be detected by an optical probe and an ultrasound probe.

The fiducial may be used to aid in image registration. For example, the fiducial may provide a geometrical and/or optical/ultrasound reference point for image registration of optical images, ultrasound images, and/or optical images together with ultrasound images. During registration between two intraoral images, each image may contain at least a portion of the fiducial (e.g., an optical image and corresponding ultrasound image each contain at least a portion of the fiducial), so the registration of the two intraoral images may have sufficient accuracy. By having known properties, a fiducial may facilitate (e.g., increase accuracy) of the registration data. Additionally, the portion of the image which includes the fiducial, or parts thereof, may be subtracted out from the scanned object, thereby leaving behind the original object's shape without the presence of the fiducial. Once the registration data is generated for the at least two images, the images may be stitched together and merged as described in reference to block 207.

Method 200 continues to block 208 where processing logic implementing the method may create a virtual model, such as a 3D virtual model, of the dental site (e.g., target area). In the case of a virtual model of a dental site, the virtual model may include all or some of the teeth, roots, gap between the roots and the bone, features of the jaw bone, and/or the alveolar canal. The 3D virtual model may be manipulated so that layers may be added or subtracted. For example, a practitioner may only want to look at the teeth and roots and may remove the jaw layer from the 3D virtual model, remove the gums from the 3D virtual model, etc. Layers may be displayed or removed from display based on one or more filter options.

Figure 3:
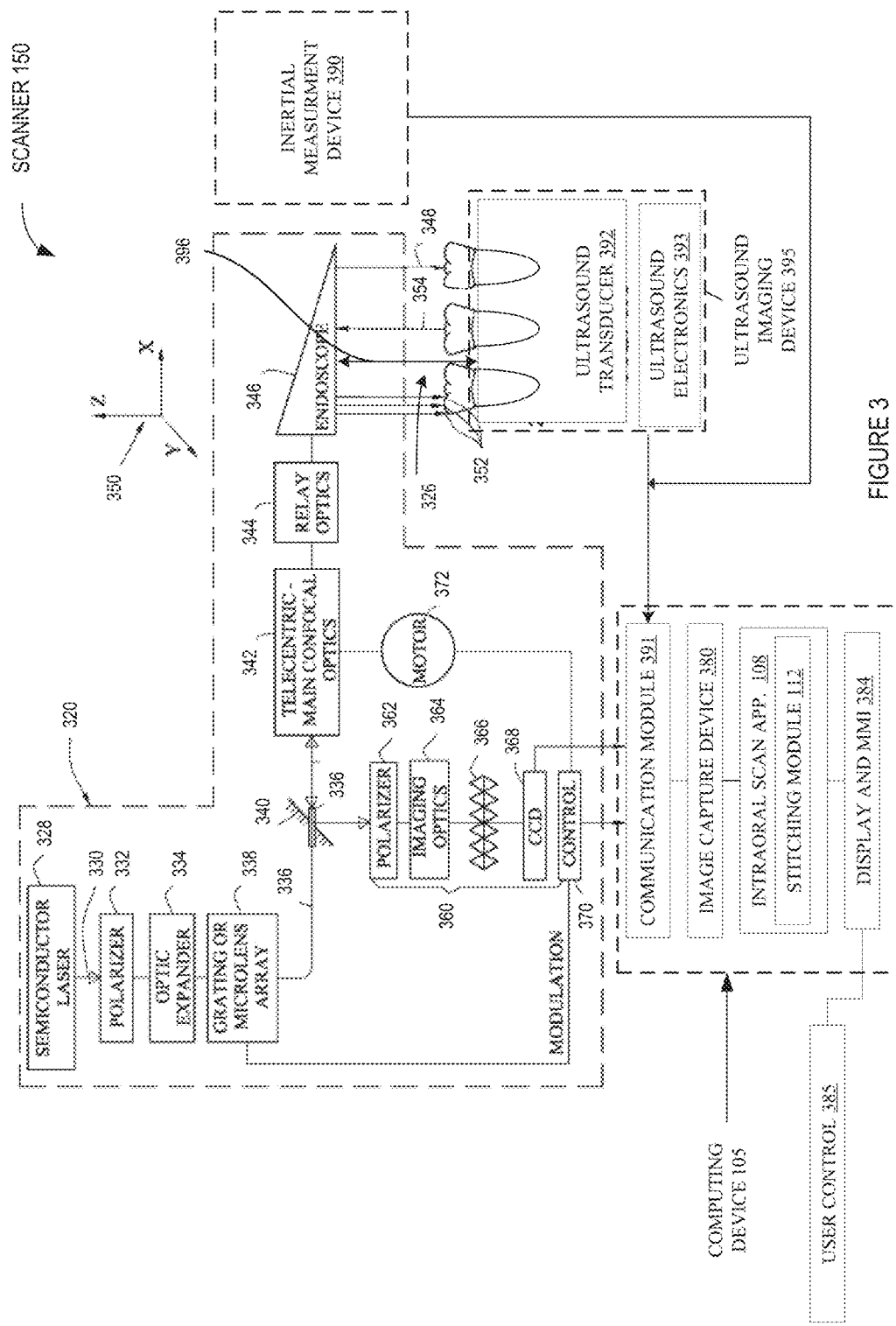
FIG. 3 illustrates a functional block diagram of an optical-ultrasound device, in accordance with embodiments of the present invention.

FIG. 3 illustrates a functional block diagram of an optical-ultrasound device, in accordance with some embodiments of the present invention. An optical-ultrasound device may be a scanner, for example scanner 150. Scanner 150 may be an intraoral scanner. Scanner 150 may include an optical imaging device 320 and ultrasound imaging device 395. For purposes of illustration, 3D axis 350 is included in FIG. 3 but may not be part of scanner 150.

Optical imaging device 320 includes a semiconductor laser 328 that emits a laser light (represented by the arrow 330). The light passes through a polarizer 332 which gives rise to a certain polarization of the light passing through polarizer 332. The light then enters into an optic expander 334 that improves the numerical aperture of the light beam 330. The light then passes through a module 338 (e.g., a grating or a micro lens array) that splits the parent beam 330 into multiple incident light beams 336, represented in FIG. 3 by a single line for ease of illustration.

The optical imaging device 320 further includes a partially transparent mirror 340 having a small central aperture. The mirror 340 allows transfer of light from the laser source through the downstream optics, but reflects light travelling in the opposite direction. In other embodiments, rather than a partially transparent mirror, other optical components with a similar function may also be used, e.g. a beam splitter. The aperture in the mirror 340 improves the measurement accuracy of the apparatus. As a result of this mirror 340, the light beams will yield a light annulus on the illuminated area of the imaged object as long as the area is not in focus and the annulus will turn into a completely illuminated spot once in focus.

Optical imaging device 320 further includes confocal optics 342 operating in a telecentric mode, relay optics 344, and an endoscope 346. In one embodiment, telecentric confocal optics avoid distance-introduced magnification changes and maintains the same magnification of the image over a wide range of distances in the Z-direction (the Z-direction being the direction of beam propagation, also referred to as the Z-axis or lens axis). The relay optics 344 allow maintenance of a certain numerical aperture of the beam's propagation.

The endoscope 346 typically includes a rigid, light-transmitting medium. The rigid, light-transmitting medium may be a hollow object defining within it a light transmission path or an object made of a light transmitting material (e.g., a glass body or tube). At its end, the endoscope typically includes a mirror of the kind ensuring a total internal reflection. The mirror may direct incident light beams towards a teeth segment 326 that is being scanned. The endoscope 346 thus emits multiple incident light beams 348 impinging on to the surface of the teeth of dental site 326.

It should be noted that scanner 150 may include a probe with a sensing face. The probe may be an end portion of scanner 150 such as a portion of optical imaging device 320 and ultrasound imaging device 395 that includes the endoscope 346 and/or ultrasound transducer 392. The optical sensor may include all or part of imaging device 320. The optical sensor 320 may alternatively be an end portion of the optical imaging device 320 that includes the endoscope 346. The probe portion of scanner 150 may be the portion of scanner 150 that extends to the dental site 326. The sensing face of scanner may be a side of the scanner 150 that is in contact with the dental site 326. For example the face of scanner 150 where endoscope 346 and ultrasound transducer 392 are directed towards dental site 326 may be the sensing face. A fixed displacement 396 is illustrated between ultrasound transducer 392 and the optical sensor (e.g., endoscope 346). In one embodiment, scanner 150 is configured such that the ultrasound transducer 392 is to be pressed against a patient's gum while the endoscope is positioned proximate to a crown of a patient's tooth. Thus, the optical imaging device 320 may generate an optical image of the tooth above the gum line, and the ultrasound imaging device may synchronously generate an ultrasound image of that same tooth below the gum line.

The incident light beams 348 form an array of light beams arranged in an X-Y plane propagating along the Z-axis. If the surface on which the incident light beams hit is an uneven surface, illuminated spots 352 are displaced from one another along the Z-axis, at different (Xi, Yi) locations. Thus, while a spot at one location may be in focus of the optical element 342, spots at other locations may be out-of-focus. Therefore, the light intensity of the returned light beams (see below) of the focused spots will be at its peak, while the light intensity at other spots will be off peak. Thus, for each illuminated spot, multiple measurements of light intensity are made at different positions along the Z-axis. For each of such (Xi, Yi) location, typically the derivative of the intensity over distance (Z) will be made, the $Z_i$ yielding maximum derivative, $Z_0$, will be the in-focus distance. As pointed out above, where, as a result of use of the partially transparent mirror 340, the incident light forms a light disk on the surface when out of focus and a complete light spot only when in focus, the distance derivative will be larger when approaching in-focus position thus increasing accuracy of the measurement.

The light scattered from each of the light spots includes a beam travelling initially in the Z-axis along the opposite direction of the optical path traveled by the incident light beams. Each returned light beam 354 corresponds to one of the incident light beams 336. Given the unsymmetrical properties of the mirror 340, the returned light beams are reflected in the direction of the detection optics 360. The detection optics 360 may include a polarizer 362 that has a plane of preferred polarization oriented normal to the plane polarization of polarizer 332. The returned polarized light beam 354 passes through an imaging optic 364, typically one or more lenses, and then through a matrix 366 including an array of pinholes. A CCD (charge-coupled device) camera 368 has a matrix of sensing elements each representing a pixel of the image and each one corresponding to one pinhole in the array 366.

The CCD camera 368 is connected to the communication module 391. Communication module 391 may coordinate the communication between and received from optical imaging device 320, ultrasound imaging device 395, inertial measurement device 390, and computing device 105. For example, communication module may synchronize the collection of data between the optical imaging device 320, the ultrasound imaging device 395, and inertial measurement device 390. Communication module 391 may be connected to image-capturing module 380 of computing device 105. Computing device 105 may be a processing device. Thus, each light intensity measurement in each of the sensing elements of the CCD camera 368 may be received and analyzed by computing device 105.

The optical imaging device 320 further includes a control module 370 connected to a controlling operation of both the semiconductor laser 328 and an actuator 372. The actuator 372 is linked to the telecentric confocal optics 342 to change the relative location of the focal plane of the confocal optics 342 along the Z-axis. In a single sequence of operation, the control module 370 induces the actuator 372 to displace the confocal optics 342 to change the focal plane location and then, after receipt of a feedback that the location has changed, the control module 370 will induce the laser 328 to generate a light pulse. At the same time, the control module 370 will synchronize the communication module 391 or image capturing module 380 to collect data representative of the light intensity from each of the sensing elements of the CCD camera 368. Then, in subsequent sequences the focal plane will change in the same manner and the data capturing will continue over a wide focal range.

The image capturing device 380 is connected to intraoral scan application 108 which then determines the relative intensity in each pixel over the entire range of focal planes of optics 342, 344. As explained above, once a certain light spot is in focus, the measured intensity will be maximal. Thus, by determining the $Z_i$, corresponding to the maximal light intensity or by determining the maximum displacement derivative of the light intensity, for each pixel, the relative position of each light spot along the Z-axis can be determined. Thus, data representative of the three-dimensional pattern of a surface in the teeth segment can be obtained. This three-dimensional representation (e.g., image) may be displayed on a display 384 and manipulated for viewing, e.g. viewing from different angles, zooming-in or out, by a user control module 385 (e.g., a computer keyboard, touchpad, mouse, etc.). In addition, the data representative of the surface topology may be transmitted through an appropriate data port, e.g. a modem, through any communication network (e.g., a local area network (LAN), wide area network (WAN), public network such as the Internet, etc.) to a recipient.

Scanner 150 may also include an inertial measurement device 390. Inertial measurement device 390 may include any combination of one or more accelerometers and/or one or more gyroscopes. Inertial measurement device 390 may include one or more magnetic sensor. The magnetic sensor may allow inertial measurement device 390 to detect the rotation position of scanner 150. The inertial measurement device 390 may be part of the probe of scanner 150. Inertial measurement device 390 may detect a rate of acceleration using one or more accelerometers and may detect changes in rotational attributes such as pitch, roll, and yaw using one or more gyroscopes. Raw inertial measurement data, such as accelerometer, gyroscope, and/or magnetic sensor data, may be sent to communication module 391. Communication module 391 may send the raw inertial measurement data to intraoral scan application 108. The raw inertial measurement data may be processed to aid in determine of the position of the probe of scanner 150, which may be used as additional input for generation of registration data. For example, intraoral scan application 108 may continually calculate the probes current position while performing intraoral scanning. For each of the six degrees of freedom, (x, y, z, θx, θy, and θz), intraoral scan application 108 may integrate over time the sensed acceleration, together with an estimate of gravity, calculate the current velocity. The current velocity may be integrated to calculate the current position.

Ultrasound imaging device 395 may include an ultrasound transducer 392 and ultrasound electronics 393. Ultrasound transducer 392 may transmit high-frequency (e.g., 1 to 20 MHz) sound pulses (e.g., sound waves or ultrasound beam) into the dental site 326. A frequency for the sound wave may be selected to provide optimal image resolution. High frequency waves may be more attenuated than low frequency waves for a given distance, but may have better resolution. The sound waves travel into the dental site 326 and impact materials with different acoustic impedances along the path of transmission. Some of the sound waves may be reflected back to ultrasound transducer 392, while some reach another material and then get reflected. The reflected waves (i.e., echoes) are detected by ultrasound transducer 392 and sent as raw ultrasound scan data to communication module 391 and eventually to intraoral scan application 108. Intraoral scan application 108 calculates the distance from the ultrasound transducer 392 to the dental site 352 using the speed of sound in a medium and the time of each echo's return. A large number, for example millions, of pulses and echoes may be sent and received each second. The ultrasound transducer 392 may be moved along the gum line and angled to obtain various views of the dental site. For example, in dental site 326 ultrasound transducer may be partially above the gum line but predominately located below the gum line to detect features hidden from the eye (and from optical imaging device 320), such as roots and jaw bone. Raw ultrasound scan data may be processed by intraoral scan application 108 to generate ultrasound images of the dental site 326.

An ultrasound transducer 392 may include one or more quartz crystals or piezoelectric crystals. Electric current may be applied to the crystals that may cause the crystals to change shape. The shape changes produce sound waves that travel outward. Conversely, when sound or pressure waves hit the crystals, the crystals may emit electrical currents. Additionally, ultrasound transducer 392 may be an array transducer including an array of individual ultrasound transducers. The array transducer may scan the target site 326 multiple times by using focused beams oriented along converging directions. The echoes from the target site may be averaged together into a single image.

Ultrasound electronics 393 may contain electronics to store, send, and receive electrical signals to ultrasound transducer 392. For instance, ultrasound electronics may include a microprocessor, memory, and amplifiers. The ultrasound electronics 393 may send electrical signals to ultrasound transducer 392 to emit sound waves, and may also receive electrical signals created from returning echoes. Additionally, the ultrasound electronics 393 may change the frequency and duration of the ultrasound signals.

Figure 4:
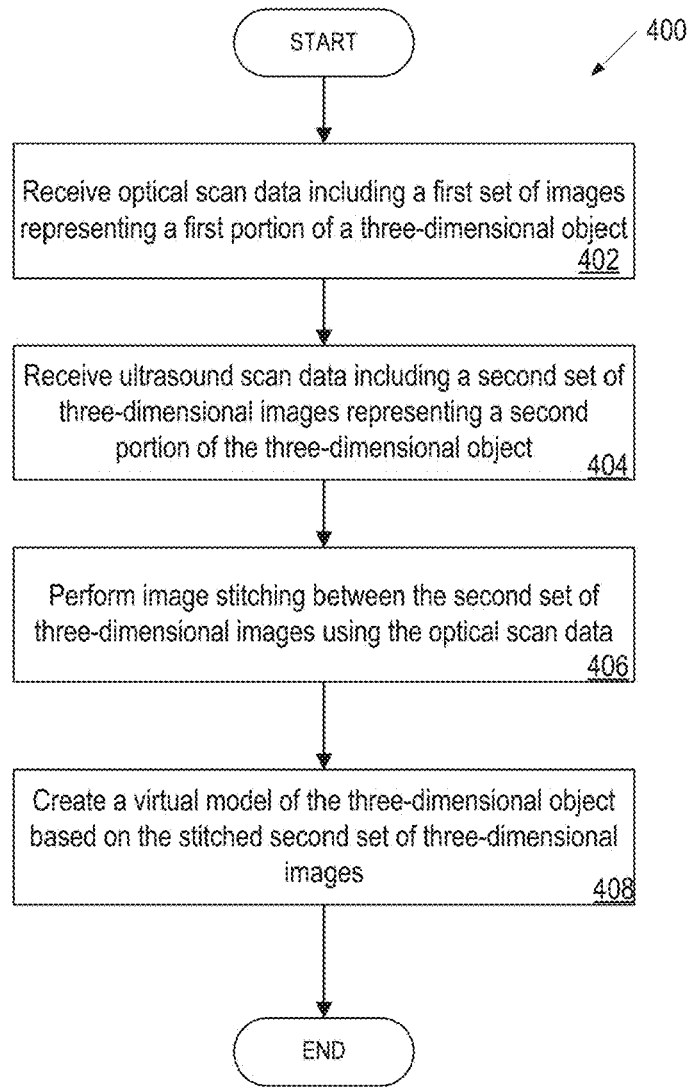
FIG. 4 illustrates a flow diagram for a method of creating a virtual model using ultrasound and optical scan data, in accordance with embodiments of the present invention.

FIG. 4 illustrates a flow diagram for a method of creating a virtual model using ultrasound and optical scan data, in accordance with embodiments of the present invention. Method 400 may be performed by processing logic that may comprise hardware (e.g., circuitry, dedicated logic, programmable logic, microcode, etc.), software (such as instructions run on a processing device), firmware, or a combination thereof. In one implementation, method 400 may be performed by system 100 of FIG. 1. In another implementation, method 400 may be performed or caused to be performed all or in part by stitching module 112 or intraoral scan application 108 of FIG. 1. For simplicity of explanation, method 400 is depicted and described as a series of acts. However, acts in accordance with this disclosure can occur in various orders, concurrently, and/or with other acts not presented or described herein. Furthermore, not all illustrated acts may be required to implement method 400 in accordance with the disclosed subject matter. In addition, those skilled in the art will understand and appreciate that method 400 may alternatively be represented as a series of interrelated states via a state diagram or interrelated events.

Method 400 begins at block 402 where processing logic implementing the method receives optical scan data including a first set of images representing a first portion of a three-dimensional object. For example, processing logic may receive raw optical scan data from scanner 150 of a dental site. The raw optical scan data may be processed to generate a set of optical images. Processing logic may receive a first set of optical images of a dental site. The three-dimensional object may be a portion of a jaw or dental arch and include crowns of one or more teeth in the jaw or dental arch. The three-dimensional object may include a coronal portion of a tooth. Coronal may mean the crown of a tooth, towards the crown of a tooth and/or related to the crown of the tooth. The optical images may be 2D images or 3D images. Block 402 may be further described with respect to FIGS. 1, 2, and 3.

Method 400 continues at block 404 where processing logic implementing the method receives ultrasound scan data including a second set of images representing a second portion of a three-dimensional object. For example, processing logic may receive raw ultrasound scan data from scanner 150 of a dental site. The raw ultrasound scan data may be processed to generate a set of ultrasound images. Processing logic may receive the ultrasound images of a dental site. The three-dimensional object may be a portion of a jaw or dental arch and include roots of one or more teeth in the jaw or dental arch. The three-dimensional object may include an apical portion of a tooth. Apical may mean tooth roots, towards the root tips of a tooth and/or related to the roots. The generation of the optical and ultrasound scan data may be approximately synchronized. The optical sensor and the ultrasound transducer may have a fixed displacement. Block 404 may be further described with respect to FIGS. 1, 2, and 3.

Method 400 continues at block 406 where processing logic performs image stitching between the second set of three-dimensional images using the optical scan data. In particular, the first set of images in the optical scan data may be registered together and/or registered to a virtual 3D model. This registration may produce registration data. The registration data from the optical images may be applied to corresponding ultrasound images in a stitching process. For example, each ultrasound image may correspond to an optical image taken at the same time as the ultrasound image. The registration data from the optical images may be used to stitch the ultrasound images to one another and/or stitch the optical images to the ultrasound images. Block 406 may be further described with respect to FIGS. 1, 2, 3, and 5.

In one embodiment, the first set of images may be a first set of two-dimensional images. Each three-dimensional image of the second set of three-dimensional images may be correlated to a two-dimensional image of the first set of two-dimensional images. For example, the optical images may be 2D optical images. Image registration may include registering the first set of 2D optical images to a pre-existing model. The registering may include determining registration data, such as rotations and translations, for one or more of the optical images that cause features in those optical images to align to similar features in the pre-existing model. For one of the more 3D images of the 3D ultrasound images, the registration data of a corresponding image from the 2D optical images may be applied in a stitching process. For example, the 2D optical images may be registered to a pre-existing model, such as a model generated from a patient's records, to generate registration data. In the stitching process, the registration data from the 2D optical images may be applied to corresponding 3D ultrasound images. Once, the 2D optical images and corresponding 3D ultrasound images have been stitched together, the resulting 3D data from the stitched images may be merged. Merging the images may smooth the transitions between the stitched images.

Figure 8:
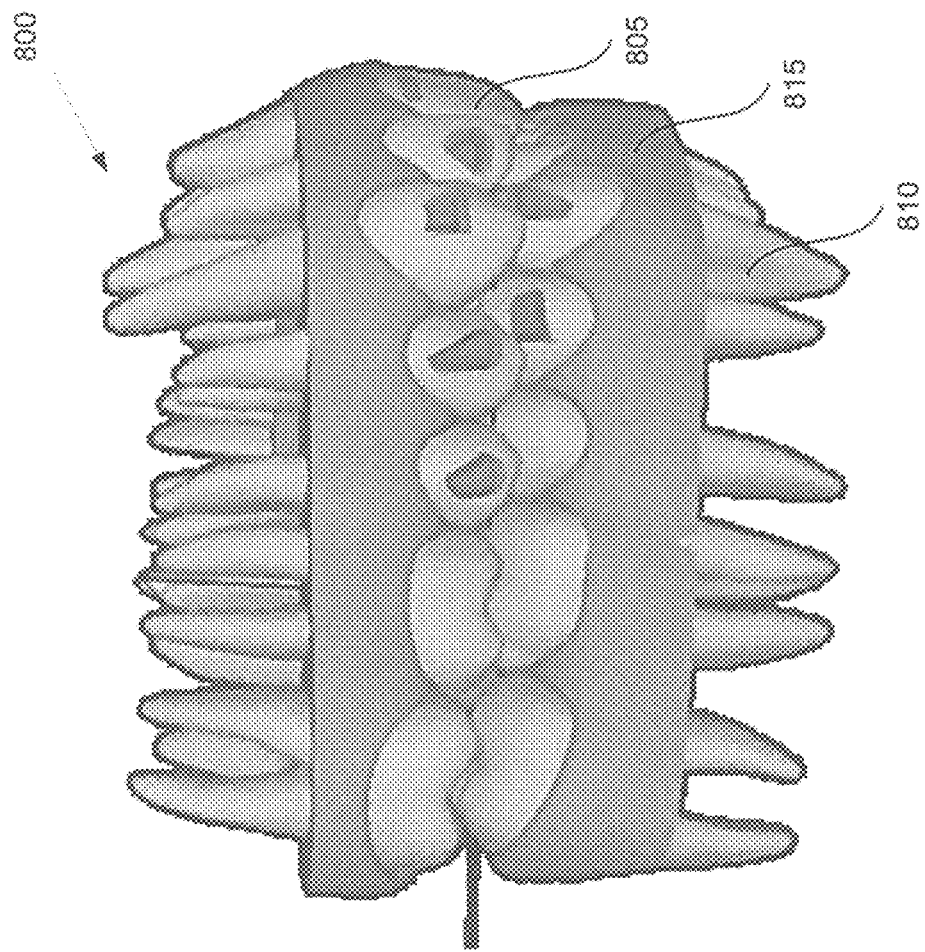
FIG. 8 is an example of a virtual model of a three-dimensional object, in accordance with embodiments of the present invention.

Method 400 continues at block 408 where processing logic creates a virtual model of the three-dimensional object based on the stitched second set of three-dimensional images. For example, the virtual model may be created of the dental site, such as crowns and roots of one or more teeth. The virtual model may be a 3D virtual model. The ultrasound images may be used to create the features below the gum line of the virtual model. For example, the ultrasound images may be used to create the roots, jaw bone, gap between the roots and jawbone. An example 3D virtual model 800 generated in accordance with method 400 is shown at FIG. 8. Block 408 may be further described with respect to FIGS. 1, 2, and 3.

Figure 5:
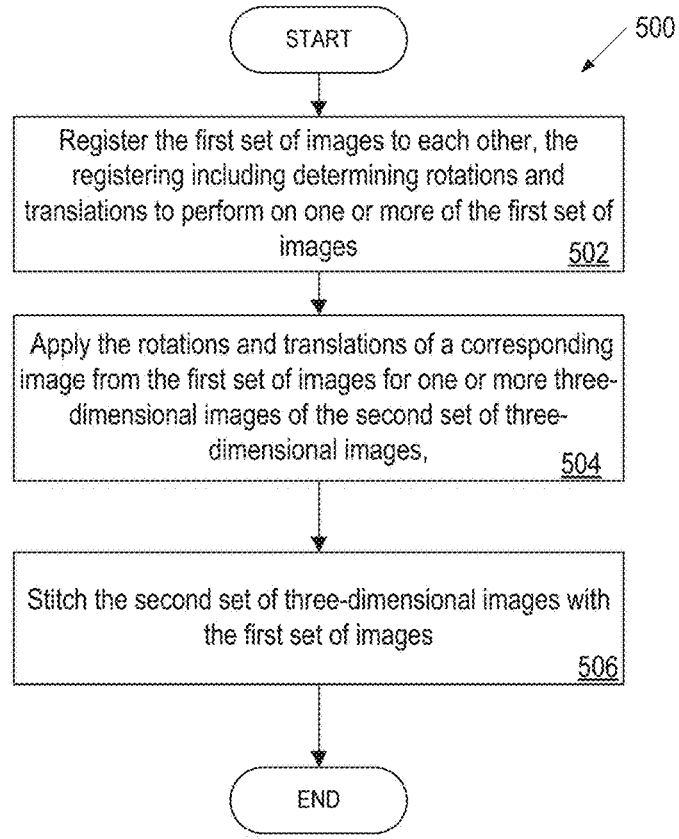
FIG. 5 illustrates a flow diagram for a method of registering and stitching ultrasound and optical images, in accordance with embodiments of the present invention.

FIG. 5 illustrates a flow diagram for a method of registering and stitching ultrasound and optical images, in accordance with embodiments of the present invention. Method 500 may be performed by processing logic that may comprise hardware (e.g., circuitry, dedicated logic, programmable logic, microcode, etc.), software (such as instructions run on a processing device), firmware, or a combination thereof. In one implementation, method 500 may be performed by system 100 of FIG. 1. In another implementation, method 500 may be performed or caused to be performed all or in part by stitching module 112 or intraoral scan application 108 of FIG. 1. For simplicity of explanation, method 500 is depicted and described as a series of acts. However, acts in accordance with this disclosure can occur in various orders, concurrently, and/or with other acts not presented or described herein. Furthermore, not all illustrated acts may be required to implement method 500 in accordance with the disclosed subject matter. In addition, those skilled in the art will understand and appreciate that method 500 may alternatively be represented as a series of interrelated states via a state diagram or interrelated events.

Method 500 begins at block 502 where processing logic implementing the method registers the first set of images to each other. The registering may include determining registration data, such as rotations and translations, to perform on one or more of the first set of optical images. For example, processing logic may register optical images together to generate registration data. Processing logic may use inertial measurement data from an inertial measurement device to improve an accuracy of the registration data and/or to improve a processing time to generate the registration data. Block 502 may be further described with respect to FIGS. 1, 2, 3, and 4.

Method 500 continues at block 504 where processing logic applies the rotations and translations of a corresponding image from the first set of images for one or more three-dimensional image of the second set of three-dimensional images. For example, processing logic may use the registration data from the optical images and apply the registration data to one or more corresponding ultrasound images. Block 504 may be further described with respect to FIGS. 1, 2, 3, and 4.

Method 500 continues at block 506 where processing logic stitches the second set of three-dimensional images with the first set of images. For example, processing logic may use the registration data for the optical images and the ultrasound images and stitch the optical and ultrasound images. Block 506 may be further described with respect to FIGS. 1, 2, 3, and 4.

Figure 6:
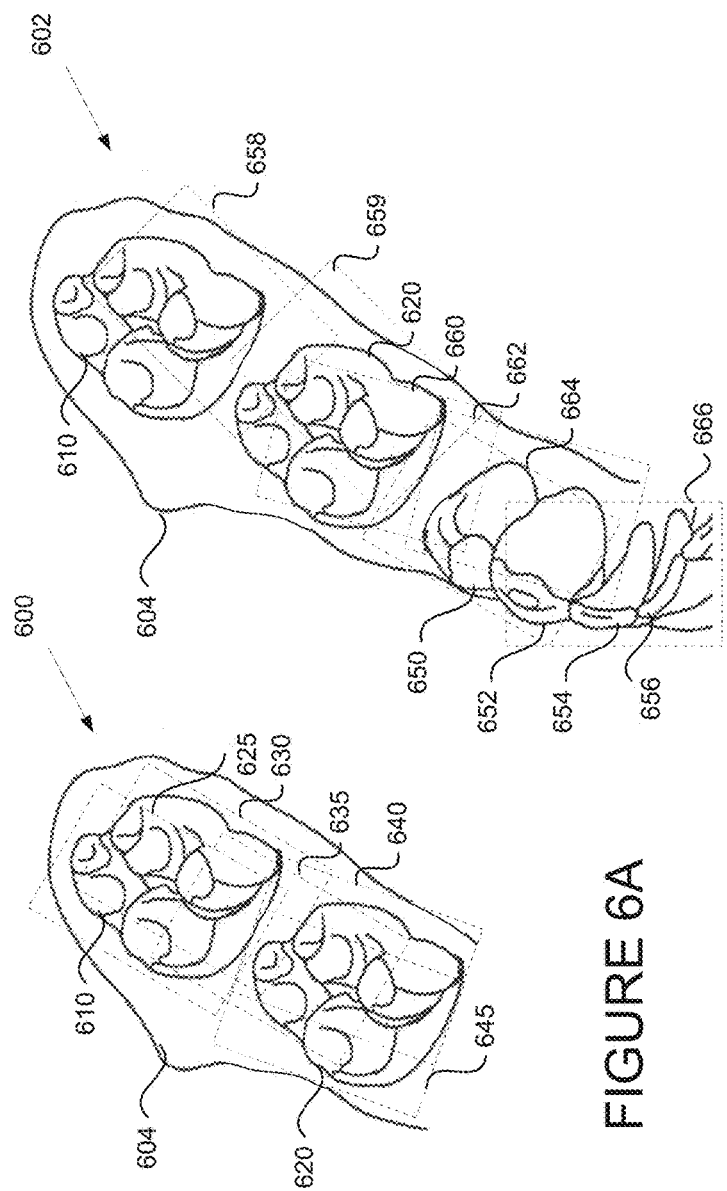
FIG. 6A illustrates a portion of an example dental arch during an intraoral scan session using optical scan data, in accordance with embodiments of the present invention.
FIG. 6B illustrates the example dental arch of FIG. 6A during the intraoral scan session after the generation of further intraoral images using optical scan data, in accordance with embodiments of the present invention.

FIG. 6A illustrates a portion of an example dental arch during an intraoral scan session using optical scan data, in accordance with embodiments of the present invention. Dental site 600 may be a scanned portion of a dental arch scanned during an intraoral scan session, in particular an optical portion of an intraoral scan. The dental site 600 includes gums 604 and multiple teeth 610, 620. Multiple optical intraoral images 625, 630, 635, 640, 645 have been taken of dental site 600 of a patient. Each of the optical intraoral images 625-645 may have been generated by an intraoral scanner having a particular distance from the dental surface being imaged. At the particular distance, the optical intraoral images 625-645 have a particular scan area and scan depth. The shape and size of the scan area will generally depend on the scanner, and is herein represented by a rectangle. Each image may have its own reference coordinate system and origin. Each intraoral image may be generated by a scanner, such as scanner 150, at a particular position (scanning station). The location and orientation of scanning stations may be selected such that together the optical intraoral images (and ultrasound intraoral images) adequately cover an entire target zone. Preferably, scanning stations are selected such that there is overlap between the intraoral images 625-645 as shown. Typically, the selected scanning stations will differ when different scanners are used for the same target area, depending on the capture characteristics of the scanner used. Thus, a scanner capable of scanning a larger dental area with each scan (e.g., having a larger field of view) will use fewer scanning stations than a scanner that is only capable of capturing 3D data of a relatively smaller dental surface. Similarly, the number and disposition of scanning stations for a scanner having a rectangular scanning grid (and thus providing projected scanning areas in the form of corresponding rectangles) will typically be different from those for a scanner having a circular or triangular scanning grid (which would provide projected scanning areas in the form of corresponding circles or triangles, respectively).

FIG. 6B illustrates the example dental arch of FIG. 6A during the intraoral scan session after the generation of further intraoral images using optical scan data, in accordance with embodiments of the present invention. Dental site 602 illustrates a scanned portion of a dental arch, which may be an update of dental site 600. Additional optical intraoral images 658, 659 have been taken to provide additional optical image data, for example for areas that were not clearly captured in FIG. 6A. Additional optical intraoral images 660, 662, 664, 666 have also been generated. These additional optical intraoral images 660-666 reveal additional features of dental site 602 such as teeth 450, 452, 454, 456. A practitioner may generate still further intraoral images as desired and to provide data for a larger target area, such as a full dental arch. While only the optical images are shown, it should be understood that each illustrated optical intraoral image is associated with a corresponding ultrasonic intraoral image that has its own scan area and scan depth.

Figure 7:
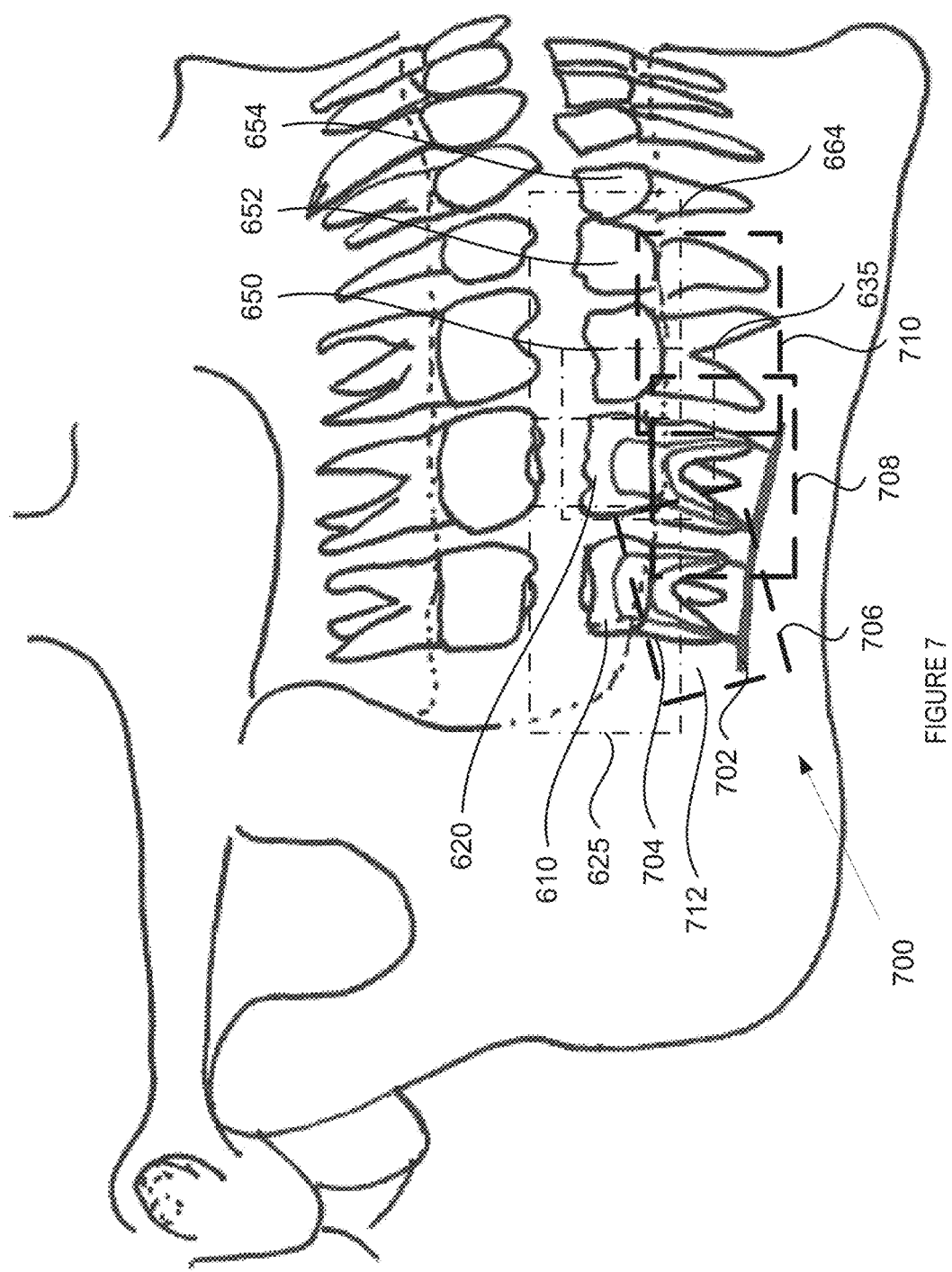
FIG. 7 illustrates an example of a patient's jaw during the intraoral scan session using ultrasound and optical scan data, in accordance with embodiments of the present invention.

FIG. 7 illustrates an example of a patient's jaw during the intraoral scan session using ultrasound and optical scan data, in accordance with embodiments of the present invention. Dental site 700 illustrates a scanned portion of a patients jaw during an intraoral scan session. Dental site 700 may be the same scanned site as dental site 600 and 602 but also includes images of features below the gum line obtained from an ultrasound scan that is synchronized to the optical scan. The intraoral scan session may include both optical and ultrasound images. The dental site 700 includes multiple teeth 610, 620, 650, 652, and 654. The dental site 700 also includes features below the gum line such as portions of the jaw bone, such as jaw bone 712, roots of teeth, such as root 704, and the alveolar canal 702. As described with respect to FIGS. 6A and 6B, multiple optical intraoral images 625, 635, 664 have been taken of dental site 700 of a patient. Additionally, multiple ultrasound intraoral images 706, 708, 710 have been taken of dental site 700 of the patient. The generation of the optical scan data and ultrasound scan data may be synchronized so that optical images may correspond with ultrasound images. For example, optical image 625 may have been synchronized with ultrasound image 706, optical image 635 may have been synchronized with ultrasound image 708, and optical image 664 may have been synchronized with ultrasound image 710. The corresponding optical and ultrasound images may have an overlapping portion which may be illustrated by the overlapping portion of the image frames. Alternatively, there may be no overlap between the corresponding optical and ultrasound images. Each of the ultrasound intraoral images 706-710 may have been generated by an intraoral scanner having a particular distance from the dental surface being imaged. In one embodiment, a probe including the ultrasound transducer is pressed against a patient's gum during imaging. Alternatively, a medium (e.g., a soft medium that may have a similar density to the gum) may be interposed between the probe of the ultrasound transducer and the gum. At the particular distance, the ultrasound intraoral images 625-645 have a particular scan area and scan depth. Each of the ultrasound intraoral images 706-710 may have been generated by an intraoral scan using a sound wave having a particular frequency. At the particular frequency, the ultrasound intraoral images 625-645 have a particular scan area and scan depth. The shape and size of the scan area will generally depend on the scanner, and is herein represented by a rectangle. Each image may have its own reference coordinate system and origin. Each intraoral image may be generated by a scanner, such as scanner 150, at a particular position (scanning station). The location and orientation of scanning stations may be selected such that together the optical intraoral images and ultrasound intraoral images adequately cover an entire target zone. Preferably, scanning stations are selected such that there is overlap between the ultrasound intraoral images 706-710 as shown. Typically, the selected scanning stations will differ when different scanners are used for the same target area, depending on the capture characteristics of the scanner used.

FIG. 8 is an example of a virtual model of a three-dimensional object, generated in accordance with embodiments of the present invention. Virtual model 800 may be 3D virtual module of the dental site 700 depicted in FIG. 7 after intraoral scans have been taken of the entire jaw. Virtual model 800 includes the both the crowns 805 and roots 810 of teeth as well as partial gums 815. Virtual model 800 may be manipulated to view dental site 700 at different angles. Virtual model 800 may also be manipulated to add or subtract different layers. In virtual model 800, the jaw bone has been removed. Additionally, the gums may be removed. Virtual model 800 may be manipulated to add the jaw bone or any other features of the dental site 700. By including ultrasound images in creating the virtual model, features below the gum line may be accurately replicated by virtual model 800.

Figure 9:
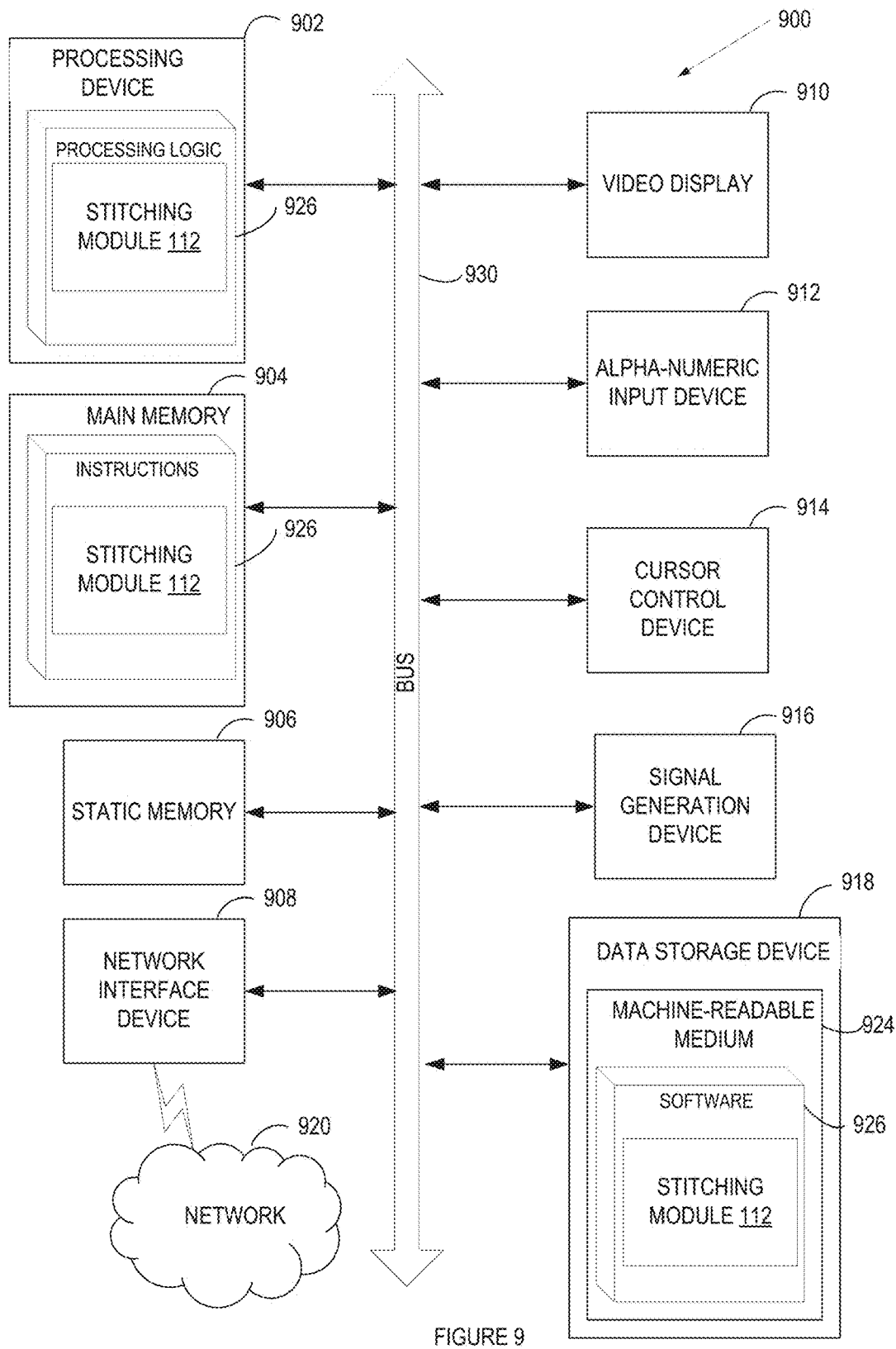
FIG. 9 illustrates a block diagram of an example computing device, in accordance with embodiments of the present invention.

FIG. 9 illustrates a block diagram of an example computing device, in accordance with embodiments of the present invention. In alternative implementations, the machine may be connected (e.g., networked) to other machines in a LAN, an intranet, an extranet, or the Internet. The machine may operate in the capacity of a server or a client device in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 900 includes a processing device 902, a main memory 904 (e.g., read-only memory (ROM), flash memory, dynamic random access memory (DRAM) (such as synchronous DRAM (SDRAM) or DRAM (RDRAM), etc.), a static memory 906 (e.g., flash memory, static random access memory (SRAM), etc.), and a data storage device 918, which communicate with each other via a bus 930.

Processing device 902 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 902 may also be one or more special-purpose processing devices such as an application specific integrated circuit (ASIC), a field programmable gate array (FPGA), a digital signal processor (DSP), network processor, or the like. The processing device 902 may be configured to execute the processing logic 926 for performing the operations and steps discussed herein.

The computer system 900 may further include a network interface device 908 communicably coupled to a network 920. The computer system 900 also may include a video display unit 910 (e.g., a liquid crystal display (LCD) or a cathode ray tube (CRT)), an alphanumeric input device 912 (e.g., a keyboard), a cursor control device 914 (e.g., a mouse), and a signal generation device 916 (e.g., a speaker).

The data storage device 918 may include a machine-accessible storage medium 924 on which may be stored software 926 embodying any one or more of the methodologies of functions described herein. The software 926 may also reside, completely or at least partially, within the main memory 904 as instructions 926 and/or within the processing device 902 as processing logic 926 during execution thereof by the computer system 900; the main memory 904 and the processing device 902 also constituting machine-accessible storage media.

The machine-readable storage medium 924 may also be used to store instructions 926 to implement the registration module 122 and/or intraoral scan application 108 to implement any one or more of the methodologies of functions described herein in a computer system, such as the system described with respect to FIG. 1, and/or a software library containing methods that call the above applications.

While the machine-accessible storage medium 924 is shown in an example implementation to be a single medium, the term "machine-accessible storage medium" should be taken to include a single medium or multiple media (e.g., a centralized or distributed database, and/or associated caches and servers) that store the one or more sets of instructions. The term "machine-accessible storage medium" shall also be taken to include any medium that may be capable of storing, encoding or carrying a set of instruction for execution by the machine and that cause the machine to perform any one or more of the methodologies of the disclosure. The term "machine-accessible storage medium" shall accordingly be taken to include, but not be limited to, solid-state memories, and optical and magnetic media.

In the foregoing description, numerous details are set forth. It may be apparent, however, that the disclosure may be practiced without these specific details. In some instances, well-known structures and devices are shown in block diagram form, rather than in detail, in order to avoid obscuring the disclosure.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "receiving", "performing", "creating", "registering", "applying", "allocating", "merging", "using", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may comprise a general purpose computer selectively activated or reconfigured by a computer program stored in the computer. Such a computer program may be stored in a machine readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems may appear as set forth in the description below. In addition, the disclosure is not described with reference to any particular programming language. It may be appreciated that a variety of programming languages may be used to implement the teachings of the disclosure as described herein.

The disclosure may be provided as a computer program product, or software, that may include a machine-readable medium having stored thereon instructions, which may be used to program a computer system (or other electronic devices) to perform a process according to the disclosure. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), etc.

Whereas many alterations and modifications of the disclosure may no doubt become apparent to a person of ordinary skill in the art after having read the foregoing description, it is to be understood that any particular example shown and described by way of illustration is in no way intended to be considered limiting. Therefore, references to details of various examples are not intended to limit the scope of the claims, which in themselves recite only those features regarded as the disclosure.

What is claimed is:

1. A method comprising:
  performing an optical scan of a tooth of a patient;
  generating three-dimensional (3D) optical scan data comprising a 3D optical image representing a coronal portion of the tooth;
  performing an ultrasonic volumetric scan on the tooth;

generating 3D volumetric scan data comprising a 3D volumetric image representing a root portion of the tooth, wherein the root portion is below a gum line of the tooth;

performing image stitching between the 3D optical image representing the coronal portion of the tooth and the 3D volumetric image representing the root portion of the tooth; and generating a virtual 3D model of the tooth based on the stitched 3D optical and 3D volumetric images.

2. The method of claim 1, further comprising:

receiving a selection of a frequency at which to perform the ultrasonic volumetric scan, wherein the selected frequency influences a vibration of the tooth.

3. The method of claim 1, wherein a frequency at which the ultrasonic volumetric scan is performed influences a resolution of the 3D volumetric image.

* * * * *